(12) United States Patent (10) Patent No.: US 12,685,690 B2
Ou (45) Date of Patent: Jul. 21, 2026

(54) EYE MASSAGER

(71) Applicant: Reestar International Limited, Hong
Kong (CN)

(72) Inventor: Yangting Ou, Hong Kong (CN)

(73) Assignee: Reestar International Limited, Hong
Kong (CN)

( * ) Notice: Subject to any disclaimer, the term of this
patent is extended or adjusted under 35
U.S.C. 154(b) by 0 days.

(21) Appl. No.: 19/023,959

(22) Filed: Jan. 16, 2025

(65) Prior Publication Data

US 2026/0199182 A1 Jul. 16, 2026

(51) Int. Cl.
*A61H 23/02* (2006.01)
*A61F 9/04* (2006.01)
*A61H 9/00* (2006.01)

(52) U.S. Cl.
CPC .............. *A61H 23/02* (2013.01); *A61F 9/04*
(2013.01); *A61H 9/0078* (2013.01); *A61H*
*2201/0134* (2013.01); *A61H 2201/165*
(2013.01); *A61H 2205/024* (2013.01); *A61H*
*2205/028* (2013.01)

(58) Field of Classification Search
CPC ................ A61F 9/04; A61H 23/00–06; A61H
2205/024; A61H 2201/165; A61H
9/00–0092; A61H 5/00–005; A61H
11/00–02; A61H 2201/1604–1607
USPC ........................................................ 601/46
See application file for complete search history.

(56) References Cited

U.S. PATENT DOCUMENTS

| | | | | | |
|---|---|---|---|---|---|
| 3,118,443 | A | * | 1/1964 | Dykinga | A61H 1/0218 |
| | | | | | D29/101.1 |
| 2016/0008209 | A1 | * | 1/2016 | Ma | A61H 7/006 |
| | | | | | 601/150 |
| 2019/0110927 | A1 | * | 4/2019 | Schwarz | A61F 9/04 |
| 2024/0173171 | A1 | * | 5/2024 | Li | A61H 23/006 |
| 2024/0261535 | A1 | * | 8/2024 | Nazarian | A61N 1/36028 |

FOREIGN PATENT DOCUMENTS

| | | | | | |
|---|---|---|---|---|---|
| CN | 108938359 | A | * | 12/2018 | ............. A61H 23/02 |
| CN | 114146313 | A | * | 3/2022 | ............. A61H 33/12 |
| CN | 117379253 | A | * | 1/2024 | ............. A61F 9/045 |
| CN | 117618228 | A | * | 3/2024 | ........... H05K 5/0204 |
| JP | 3246481 | U | * | 4/2024 | ............. A61F 9/04 |
| KR | 20220150494 | A | * | 11/2022 | ........... A61H 23/006 |
| KR | 20240081593 | A | * | 6/2024 | ............. A61H 39/04 |

OTHER PUBLICATIONS

Translation of CN 108938359. Accessed from PE2E-Search on Aug.
28, 2025. (Year: 2018).*

(Continued)

*Primary Examiner* — Paige Kathleen Bugg

(57) ABSTRACT

An eye massager includes: an eye mask assembly, including
a flexible eye mask body configured to cover eyes of a user
to shield light from the eyes; and a massaging assembly. The
massaging assembly and the flexible eye mask body are
selectively in an assembled state or a separate state. When
the massaging assembly and the flexible eye mask body are
in the assembled state, the eye massager is configured to
massage at least one of: an eye region, an eye peripheral
region, and temples of the user.

19 Claims, 24 Drawing Sheets

100

(56)    References Cited

OTHER PUBLICATIONS

Translation of CN 114146313. Accessed from PE2E-Search on Aug. 28, 2025. (Year: 2022).*

Translation of CN 117379253. Accessed from PE2E-Search on Aug. 28, 2025. (Year: 2023).*

Translation of CN 117618228. Accessed from PE2E-Search on Aug. 28, 2025. (Year: 2024).*

Translation of JP 3246481. Accessed from PE2E-Search on Aug. 28, 2025. (Year: 1999).*

Translation of KR 2022/0150494. Accessed from PE2E-Search on Aug. 28, 2025. (Year: 2022).*

Translation of KR 2024/0081593. Accessed from PE2E-Search on Jan. 14, 2026. (Year: 2024).*

* cited by examiner

106

2060

20600

2048

20480

EYE MASSAGER

TECHNICAL FIELD

The present disclosure relates to the field of massagers, and in particular to an eye massager.

BACKGROUND

As people pay increasing attention to health, massagers are favored by many people. An eye massager is a device for massaging human eyes, eye regions and temples. The eye massager in the art, having a massaging and light shielding effect, is heavy in weight. Therefore, when a user needs the light shielding effect without the massaging effect (such as during sleeping), the eye massager may not be used conveniently, and the user experience is poor.

Therefore, it is an urgent problem of how to improve the eye massager to enable the user to use the eye massager flexibly according to an application scenario so as to improve the user experience.

SUMMARY OF THE DISCLOSURE

The present disclosure provides an eye massager, including: an eye mask assembly, including a flexible eye mask body configured to cover eyes of a user to shield light from the eyes; and a massaging assembly. The massaging assembly and the flexible eye mask body are selectively in an assembled state or a separate state. When the massaging assembly and the flexible eye mask body are in the assembled state, the eye massager is configured to massage at least one of: an eye region, an eye peripheral region, and temples of the user.

BRIEF DESCRIPTION OF THE DRAWINGS

In order to more clearly illustrate technical solutions in the embodiments or in the related art of the present disclosure, accompanying drawings for describing the embodiments or the related art will be briefly introduced below. Apparently, the accompanying drawings in the following description show only some of the embodiments of the present disclosure, and any ordinary skilled person in the art may obtain other drawings based on the following accompanying drawings without any creative work.

REFERENCE NUMERALS IN THE DRAWINGS

Figure 1:
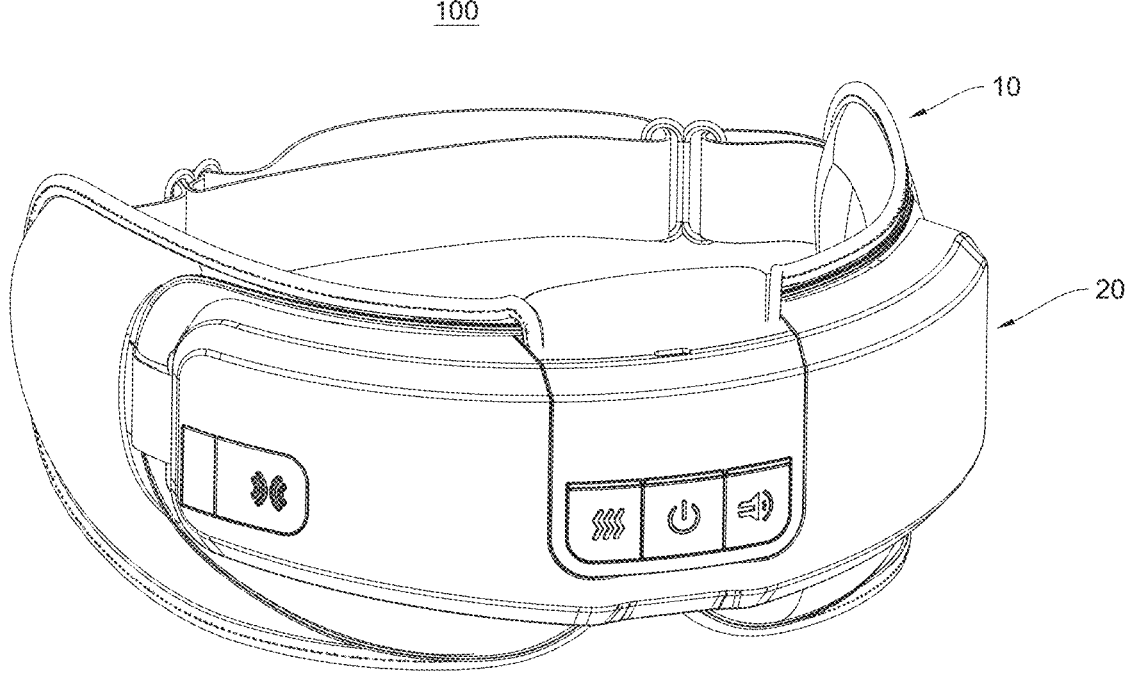
FIG. 1 is a structural schematic view of an eye massager after being assembled according to an embodiment of the present disclosure.

100—eye massager; 10—eye mask assembly; 101—middle portion; 102—flexible eye mask body; 1020—pocket structure; 10200—opening; 10202—interlayer; 1022—first body portion; 1024—second body portion; 10240—opening; 1025—lower edge; 103—left side; 104—right side; 105—receiving space; 106—power supply module; 1062—first shell; 1063—left side; 10620—guide groove; 10622—protrusion; 10624—protruding portion; 1064—battery; 1065—right side; 1066—first PCBA board; 1068—ejecting post base; 10680—flange; 107—connection portion; 108—heating structure; 110—speaker; 112—fixing strap; 114—cushioning portion; 20—massaging assembly; 200—left side; 201—right side; 202—air bag module; 2020—base; 20202—left end; 20204—right end; 2021—first side; 2022—air bag; 203—middle portion; 204—air bag drive module; 2040—air pump; 2041—air valve; 2042—second shell; 2043—second PCBA board; 2045—vibration motor; 2046—power supply adapter PCBA board; 2047—left side; 2048—ejecting post set; 20480—concave edge; 2049—right side; 206—recess; 2060—guiding protrusion; 20600—recess opening; 2061—top side; 2062—rear side wall; 2063—front side; 2064—bottom wall; 2065—snap slot; 2066—left side wall; 2068—right side wall; 30—first connection member; 40—second connection member; 50—first Velcro sticker; 60—second Velcro sticker; D—extending direction.

DETAILED DESCRIPTION

In order to make objectives, technical solutions and advantages of the embodiments of the present disclosure clearer, the technical solutions in the embodiments of the present disclosure will be described clearly and completely in the following by referring to the accompanying drawings. Apparently, the described embodiments show only some, but not all of, embodiments of the present disclosure. All other embodiments, which are obtained by any ordinary skilled person in the art based on the embodiments described herein without creative work, shall fall within the scope of the present disclosure.

It should be noted that all directional indications (such as up, down, left, right, front, rear, top, bottom) in the embodiments of the present disclosure are used only for explaining relative positional relationships and movements among various components at a particular attitude (the attitude as shown in the accompanying drawings). The directional indications may be correspondingly changed when the particular attitude is changed. In the embodiments of the present disclosure, terms such as "first", "second", and the like are used for descriptive purposes only, and shall not be interpreted as indicating or implying relative importance or specifying the number of technical features. Therefore, a feature defined by the "first" or "second" may include at least one such feature, either explicitly or implicitly.

In order to enable any ordinary skilled person in the art to better understand the embodiments of the present disclosure, the technical solutions in the embodiments of the present disclosure will be clearly and completely described below by referring to the accompanying drawings.

Figure 2:
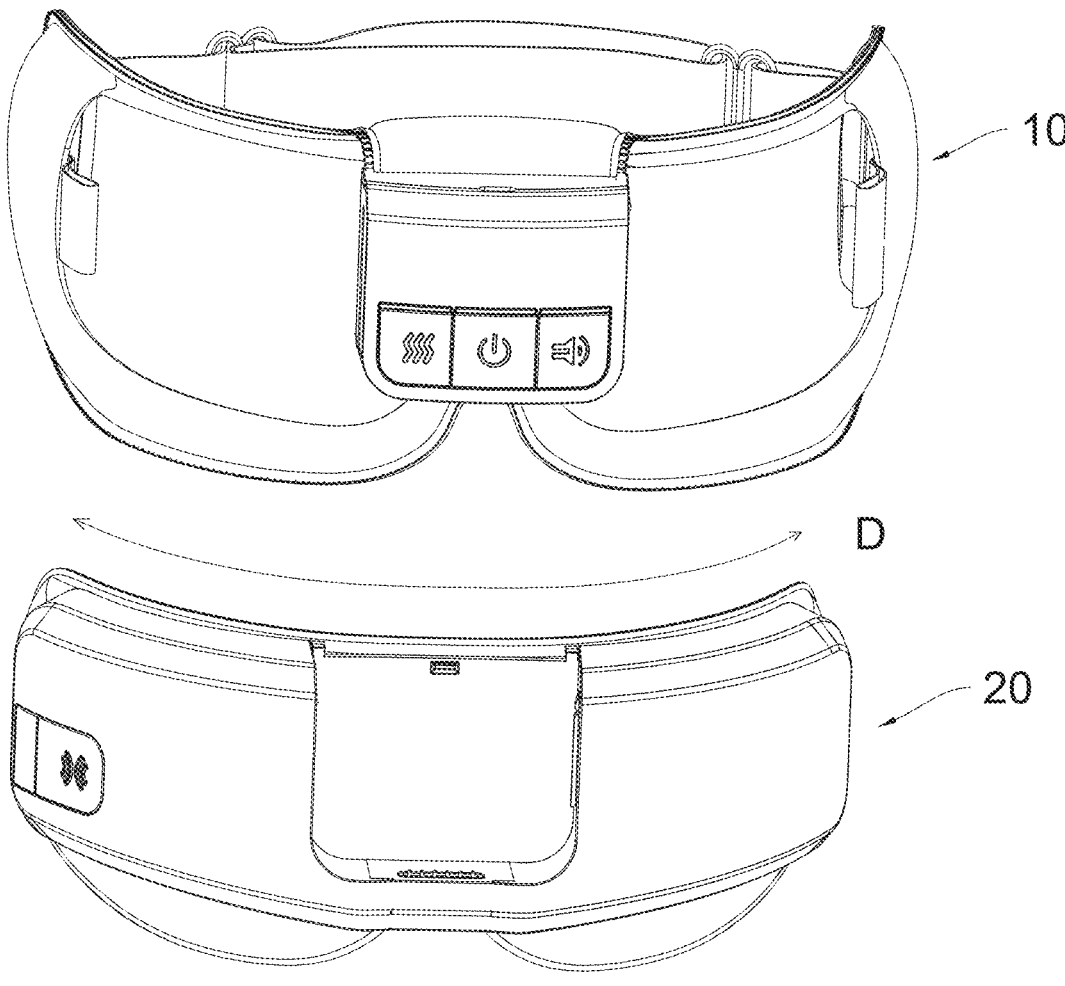
FIG. 2 is a structural schematic view of the eye massager after being disassembled according to an embodiment of the present disclosure.
Figure 3:
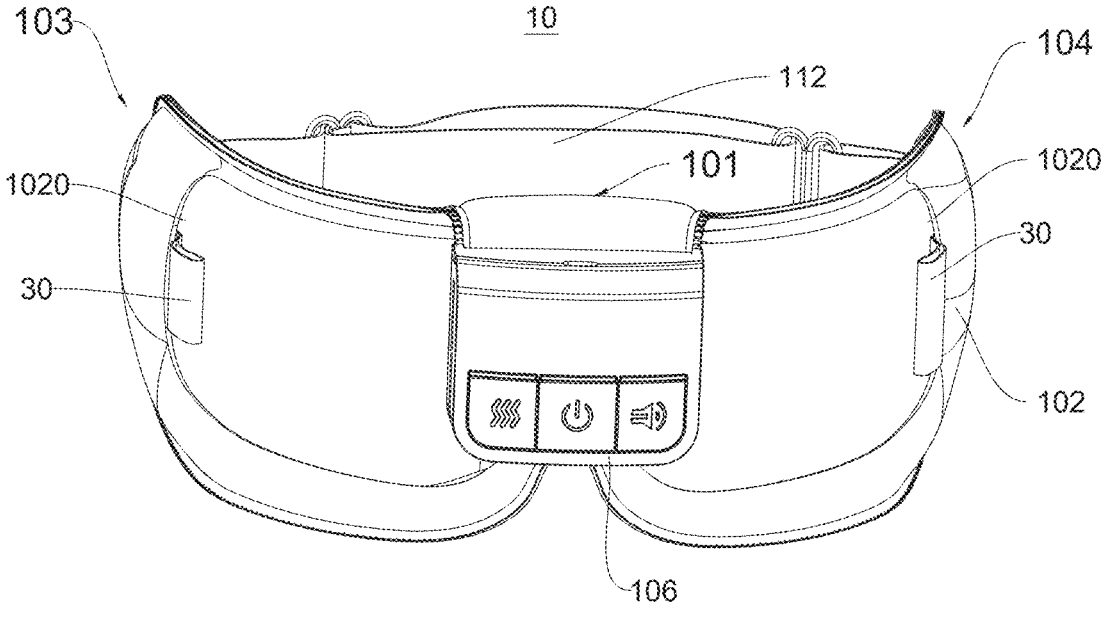
FIG. 3 is a structural schematic view of an eye mask assembly shown in FIG. 2 being viewed from a viewing angle.

As shown in FIG. 1, the present disclosure provides an eye massager 100. As shown in FIGS. 2-3, the eye massager 100 may include an eye mask assembly 10 and a massaging assembly 20. The eye mask assembly 10 includes a flexible eye mask body 102 configured to cover eyes of a user to shield light from the eyes. The massaging assembly 20 and the flexible eye mask body 102 may be selectively in an assembled state (as shown in FIG. 1) or a separate state (as shown in FIG. 2). When the massaging assembly 20 and the flexible eye mask body 102 are in the assembled state (as shown in FIG. 1), the eye massager 100 may be configured to massage an eye region, an eye peripheral region, and the temples of the user. For the eye massager 100 in the present disclosure, since the eye mask assembly 10 and the massaging assembly 20 are selectively in the assembled state or in the separate state, the user may use the eye mask assembly 10 alone in a case where eye massaging is not required. For example, when the user is sleeping, only a light shielding effect is needed. Therefore, the massaging assembly 20 and the flexible eye mask body 102 can be separated from each other, and the eye mask assembly 10 is used alone. In this way, inconvenience to the user, caused by a large overall weight due to the eye mask assembly 10 and the massaging assembly 20 being assembled with each other, can be avoided. Therefore, the eye massager 100 of the present disclosure can be expanded to a variety of usage scenarios, and the user experience is improved.

Figure 11:
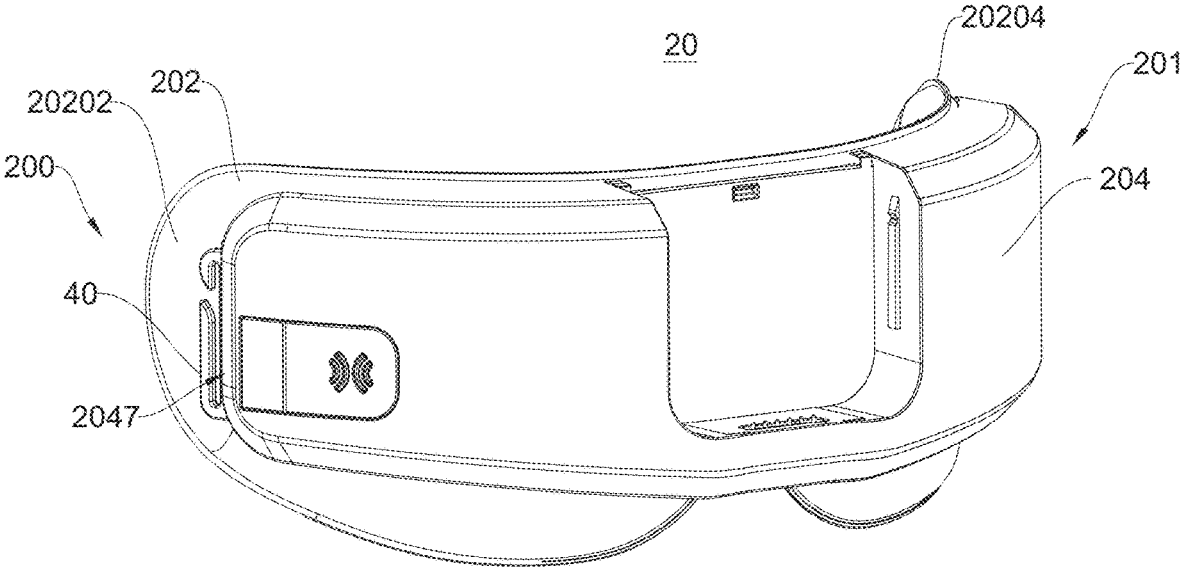
FIG. 11 is a structural schematic view of a massaging assembly shown in FIG. 2 being viewed from a viewing angle.
Figure 12:
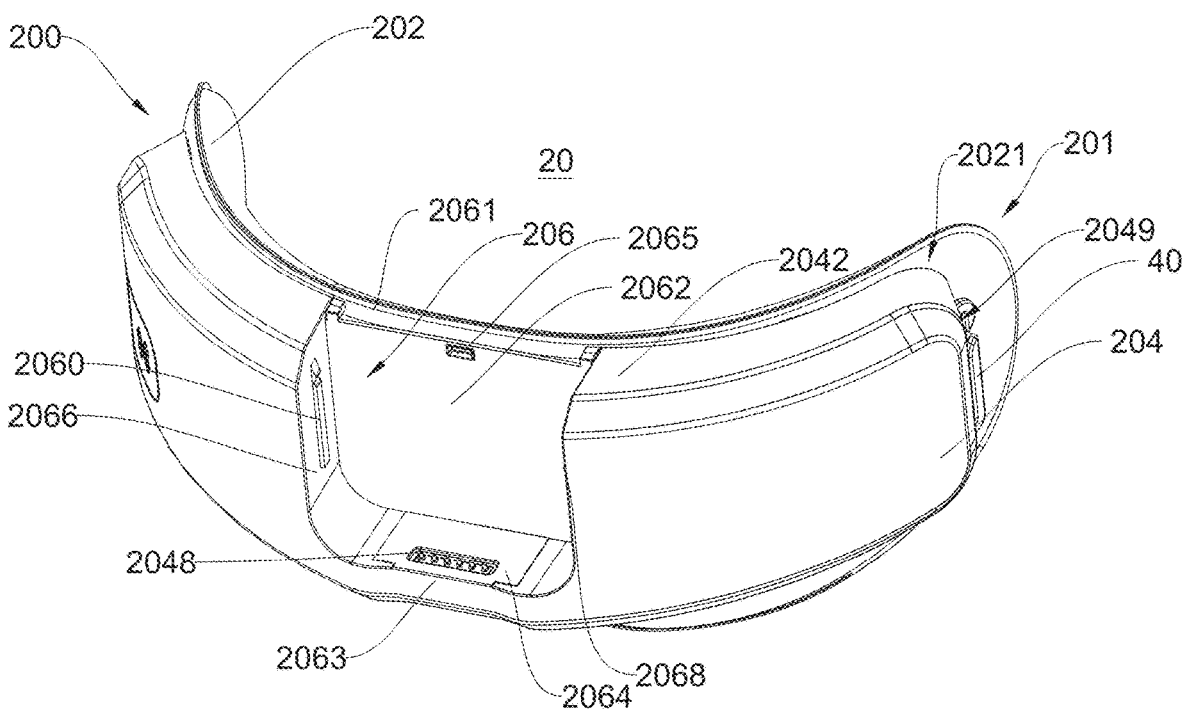
FIG. 12 is a structural schematic view of the massaging assembly shown in FIG. 2 being viewed from another viewing angle.

As shown in FIGS. 1 and 2, the flexible eye mask body 102 and the massaging assembly 20 are arranged transversely to be attached to the eyes of the user, extending along an extending direction D. In an embodiment, the flexible eye mask body 102 and the massaging assembly 20 are detachably connected to each other via a connection member. When the flexible eye mask body 102 and the massaging assembly 20 are connected to each other via the connection member, the massaging assembly 20 and the flexible eye mask body 102 can be tightly attached to each other. As shown in FIG. 3 and FIGS. 11-12, one first connection member 30 is arranged on each of a left side 103 and a right side 104 of the flexible eye mask body 102, and one second connection member 40 is arranged on each of a left side 200 and a right side 201 of the massaging assembly 20. The first connection member 30 on the left side 103 of the flexible eye mask body 102 and the second connection member 40 on the left side 200 of the massaging assembly 20 are detachably connected to each other; and the first connection member 30 on the right side 104 of the flexible eye mask body 102 and the second connection member 40 on the right side 201 of the massaging assembly 20 are detachably connected to each other. In this way, the eye mask assembly 10 and the massaging assembly 20 can be selectively in the assembled state or in the separate state. In the above embodiment, by arranging two first connection members 30 and two second connection members 40 respectively on the flexible eye mask body 102 and the massaging assembly 20 and the two first connection members 30 and the two second connection members 40 are detachably connected to each other correspondingly, the eye mask assembly 10 and the massaging assembly 20 are selectively configured in the assembled state or in the separate state. The user may use the eye massager 100 conveniently, the user experience is improved. In the assembled state, a distance along the extending direction D is formed between the first connection member 30 and the second connection member 40 on a same side, the massaging assembly 20 and the flexible eye mask body 102 can be tightly stretched. In this way, an outward push of the massage assembly 20 after being inflated is converted into an inward push pressure applied by the flexible eye mask body 102 on the eyes and the temples of the user, such that the eyes and a head can be comfortably and effectively massaged and relaxed. To be noted that, each of the number of first connection members 20 and the number of second connecting members 40 is not limited to two and may be three or more, as long as the eye mask assembly 10 and the massaging assembly 20 can be detachably connected to each other. The present disclosure does not limit the number of first connection members 30 and the number of second connection members 40. Further, in an example, the first connection member 30 may be a pullable strap and the second connection member 40 may be a pull ring having an opening, or vice versa. Specifically, the pullable strap may be a striped and ring-shaped strap having two openings respectively at two sides (as shown in FIGS. 2-3). The pull ring is a ring-shaped structure having a notch (as shown in FIG. 11). When the eye mask assembly 10 with the massaging assembly 20 are assembled to each other, the pull ring sleeves the pullable strap via the notch of the pull ring and the openings of the pullable strap, such that the eye mask assembly 10 to the massaging assembly 20 are connected to each other.

Figure 8:
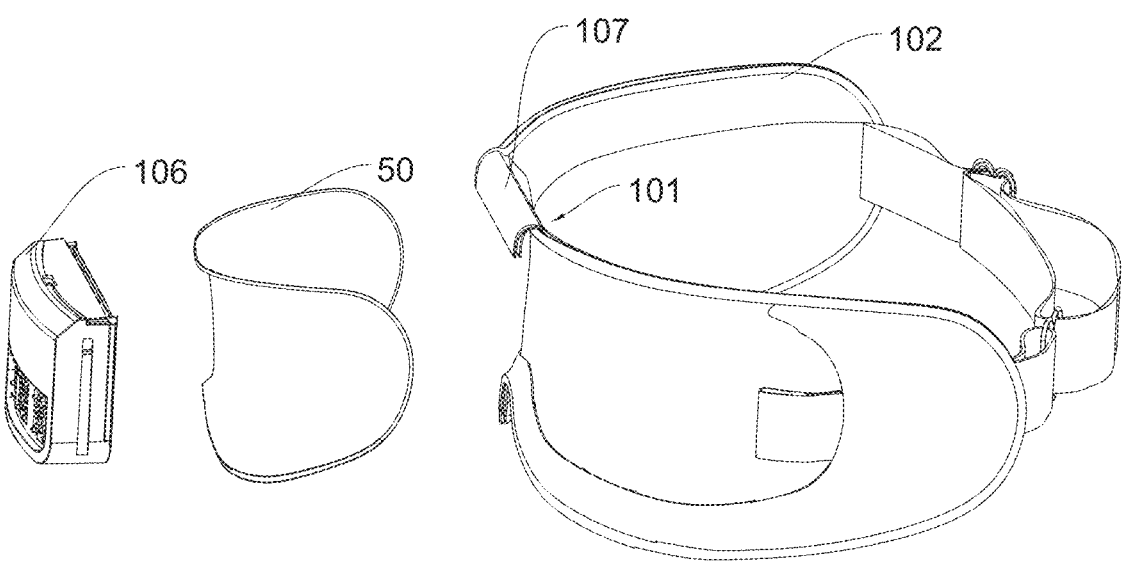
FIG. 8 is a structural schematic view of the eye mask assembly after being disassembled according to another embodiment of the present disclosure.
Figure 15:
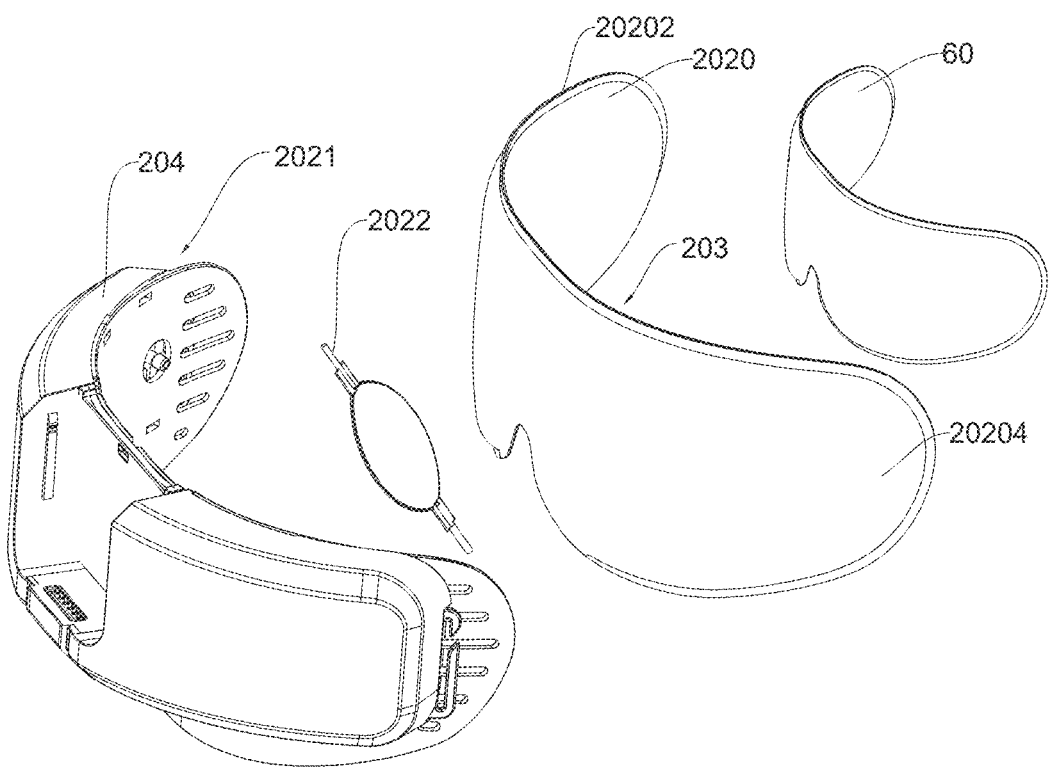
FIG. 15 is an exploded view of the massaging assembly according to an embodiment of the present disclosure.

Further, in addition to taking connection members to achieve detachable connection between the eye mask assembly 10 and the massaging assembly 20, in some embodiments, the detachable connection of the eye massager 100 of the present disclosure can be achieved by arranging Velcro stickers. Specifically, as shown in FIGS. 8 and 15, the flexible eye mask body 102 is arranged with a first Velcro sticker 50, and the massaging assembly 20 is arranged with a second Velcro sticker 60. The first Velcro sticker 50 and the second Velcro sticker 60 are disposed opposite to each other to enable the flexible eye mask body 102 and the massaging assembly 20 to be detachably adhered to each other. Of course, in the eye massager 100 of the present disclosure, the connection members and the Velcro stickers may all be arranged to achieve the detachable connection. In this case, the first Velcro sticker 50 is disposed at a middle portion 101 of the flexible eye mask body 102, and the second Velcro sticker 60 is disposed at a middle portion 203 of the massaging assembly 20, such that the middle portion 101, the left side 103 and the right side 104 of the flexible eye mask body 102 can all be completely adhered to the massaging assembly 20, and the inward push pressure of the massaging assembly 20 can be better transferred.

Figure 5:
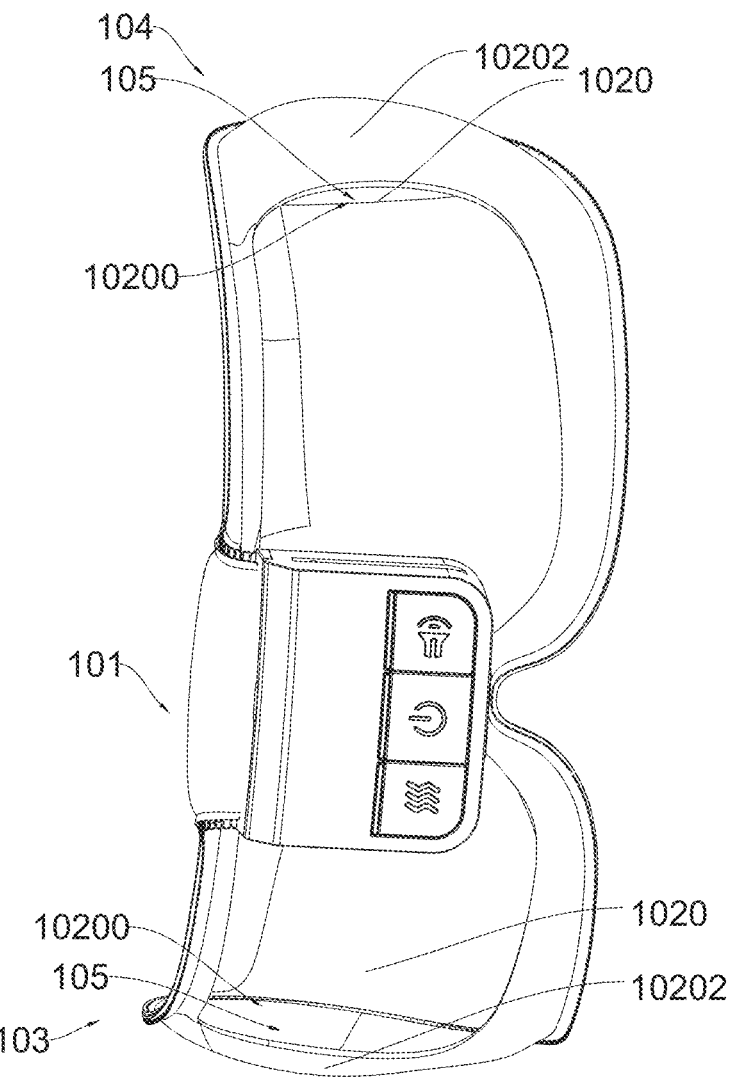
FIG. 5 is a structural schematic view of the eye mask assembly shown in FIG. 2 being viewed from still another viewing angle.
Figure 6:
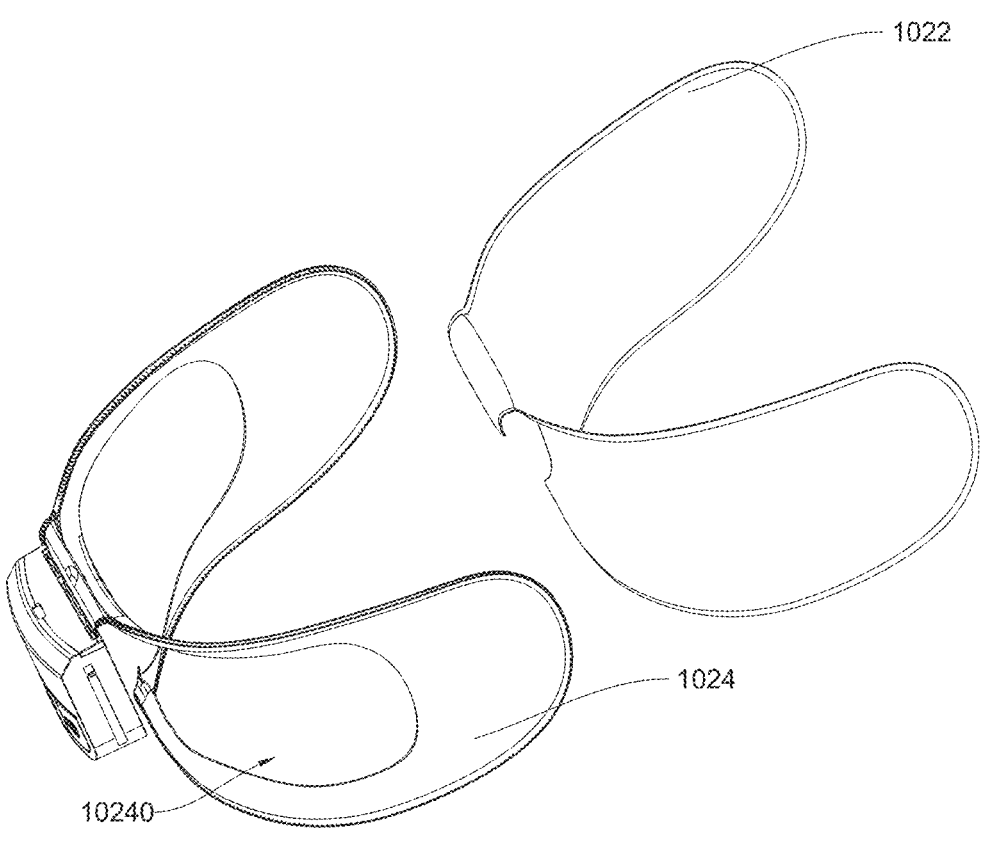
FIG. 6 is a structural schematic view of the eye mask assembly after being disassembled according to an embodiment of the present disclosure.

As shown in FIGS. 3 and 5, each of the left side 103 and the right side 104 of the flexible eye mask body 102 is further arranged with a pocket structure 1020. The pocket structure 1020 is opened towards the middle portion 101 of the flexible eye mask body 102 to form a receiving space 105 having an opening 10200. Specifically, a shape of an opening 10200 of the pocket structure 1020 at the left side matches with a shape of the left side 200 of the massaging assembly 20; and a shape of an opening 10200 of the pocket structure 1020 at the right side matches with a shape of the right side 201 of the massaging assembly 20 (as shown in FIG. 11). For example, the openings and the left side 200 and the right side 201 of the massaging assembly 20 are curved or in other shapes. When the two first connection members 30 and the two second connection members 40 are connected to each other in one-to-one correspondence, the left side 200 and the right side 201 of the massaging assembly 20 are respectively at least partially inserted in the respective receiving space 105. In an embodiment, as shown in FIG. 6, the flexible eye mask body 102 includes a first body portion 1022 and a second body portion 1024. The first body portion 1024 defines an opening 10240. The first body portion 1022 is recessed towards an inner side of the eye mask assembly 10, and the second body portion 1024 is protruding towards an outer side of the eye. mask assembly 10. In this way, when the first body portion 1022 and the second body portion 1024 are assembled to each other, one pocket structure 1020 is formed at each of the left side 103 and the right side 104 of the flexible eye mask body 102. As shown in FIG. 3, two first connection members 30 are at least partially received in two pocket structures 1020, respectively. In the present embodiment, the eye mask assembly 10 and the massaging assembly 20 are tightly connected to each other by arranging the connection members respectively on the left side and the right side of the flexible eye mask body 102 and on the left side and the right side of the massaging assembly 20, and the left side and the right side of the massaging assembly 20 are at least partially inserted in the respective receiving space of the eye mask assembly 10. In this way, assembling between the massaging assembly 20 and the eye mask assembly 10 is invisible, such that in the assembled state, a more aesthetic appearance is achieved. In addition, two pocket structures 1020 respectively receive the left side and the right side of the eye mask assembly 10. Therefore, in the assembled state, movements of the eye mask assembly 10 is limited, and arrangement of the first connection members 30 and the second connection members 40 enables the outward push of the massaging assembly 20 after being inflated to be converted into the inward push pressure to be applied on the eyes and the temples of the user.

As shown in FIG. 11, the massaging assembly 20 includes an air bag module 202 and an air bag drive module 204. The air bag module 202 is disposed facing towards the flexible eye mask body 102, and the air bag drive module 204 is disposed on a first side 2021 of the air bag module 202 away from the flexible eye mask body 102 (shown in FIG. 12) and is attached to the air bag module 202. In some embodiments, as shown in FIGS. 11 and 12, the two second connection members 40 are respectively arranged at a left side 2047 and a right side 2049 of the air bag drive module 204. An extending length of a base 2020 in the extending direction D is greater than an extending length of the air bag drive module 204 in the extending direction D. In this way, a left end 20202 and a right end 20204 of the base 2020 can be inserted respectively in the two pocket structures 1020. An air bag 2022 is arranged inside the base 2020. Since the base 2020 is longer than the air bag drive module 204, a space occupied by the air bag 2022 in the base 2020 is increased, such that a massaging area of the eye massager 100 is increased, and the distance between the first connection member 30 and the second connection member 40 is provided. The air bag drive module 204 is shortened, so as to reduce an overall weight of the eye massager 100.

In an embodiment, the second connection member 40 is the pull ring having a hole. The air bag drive module 204 includes a shell, the shell is arranged with a connection post. The connection post passes through the hole in the pull ring to enable the second connection member 40 and the air bag drive module 204 to be fixedly connected to each other. The first connection member 30 is the pullable strap and is sewn directly into the pocket structure 1020. In this way, manufacturing costs are saved, and a manufacturing process is simplified.

Figure 4:
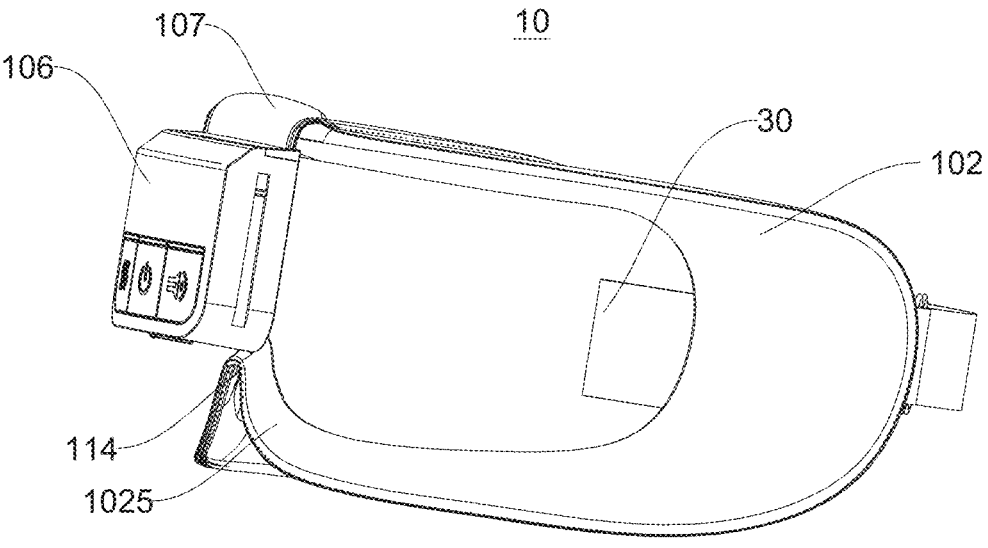
FIG. 4 is a structural schematic view of the eye mask assembly shown in FIG. 2 being viewed from another viewing angle.

As shown in FIG. 3, the eye mask assembly 10 further includes a power supply module 106. The power supply module 106 is connected to the flexible eye mask body 102. Specifically, as shown in FIGS. 3-4, the power supply module 106 and the flexible eye mask body 102 are connected to each other via a connection portion 107. The connection portion 107 is disposed at a middle portion 101 of the flexible eye mask body 102. The power supply module 106 is disposed at a middle portion of the flexible eye mask body 102. As shown in FIG. 15, the air bag module 202 includes the base 1020 and the air bag 2022 arranged in the base 2020. The air bag drive module 204 is configured to inflate and deflate the air bag 2022. As shown in FIG. 12, the air bag drive module 204 defines with a recess 206. The power supply module 106 is detachably received in the recess 206 to be electrically connected to the air bag drive module 204. In some embodiments, the power supply module 106 is hexahedral (as shown in FIG. 3). The air bag drive module 204 is a strip-shaped structure having the recess at a middle. A shape of the recess matches a shape of the power supply module 106. In this way, the power supply module 106 can be tightly connected with the air bag drive module 204 when the eye mask assembly 10 and the massaging assembly 20 are in the assembled state, preventing the power supply module 106 and the air bag drive module 204 from being separated from each other. As described below, a heating sheet and a speaker may be arranged in the eye mask assembly 10. When the eye mask assembly 10 and the massaging assembly 20 are in the separate state, the power supply module 106 can supply power to and control the heating sheet and the speaker. In this way, when the eye mask assembly 10 is used alone, such as during sleeping, light shielding, heating and music playing for relaxation can be achieved, quality of sleeping can be improved. When the eye mask assembly 10 and the massaging assembly 20 are in the assembled state, the power supply module 106 can supply power to the massaging assembly 10 to achieve massaging.

Figure 10:
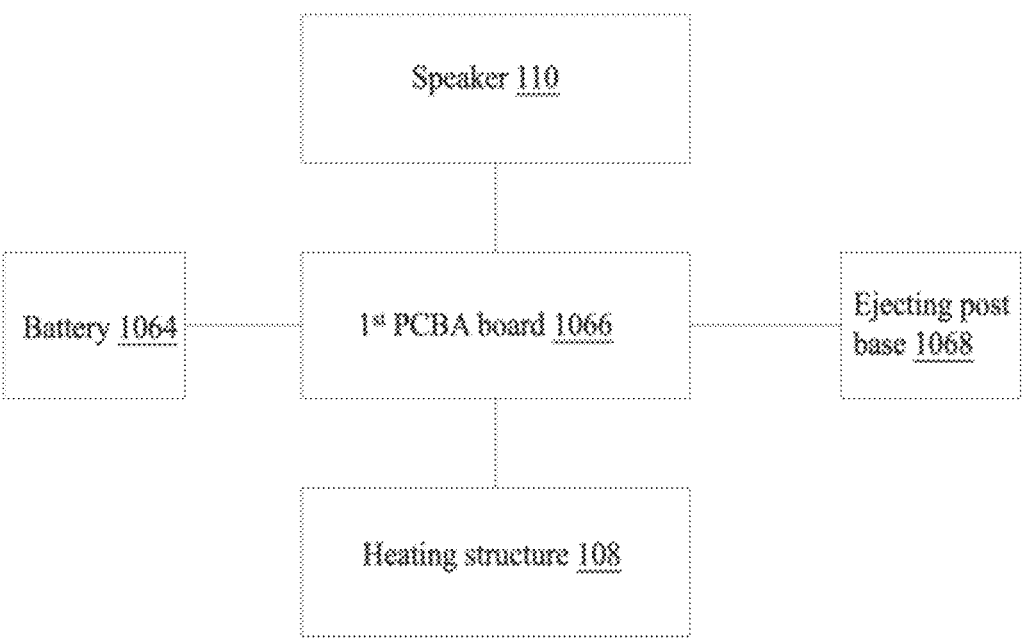
FIG. 10 is a structural schematic view of connection between internal components of the eye mask assembly according to an embodiment of the present disclosure.
Figure 16:
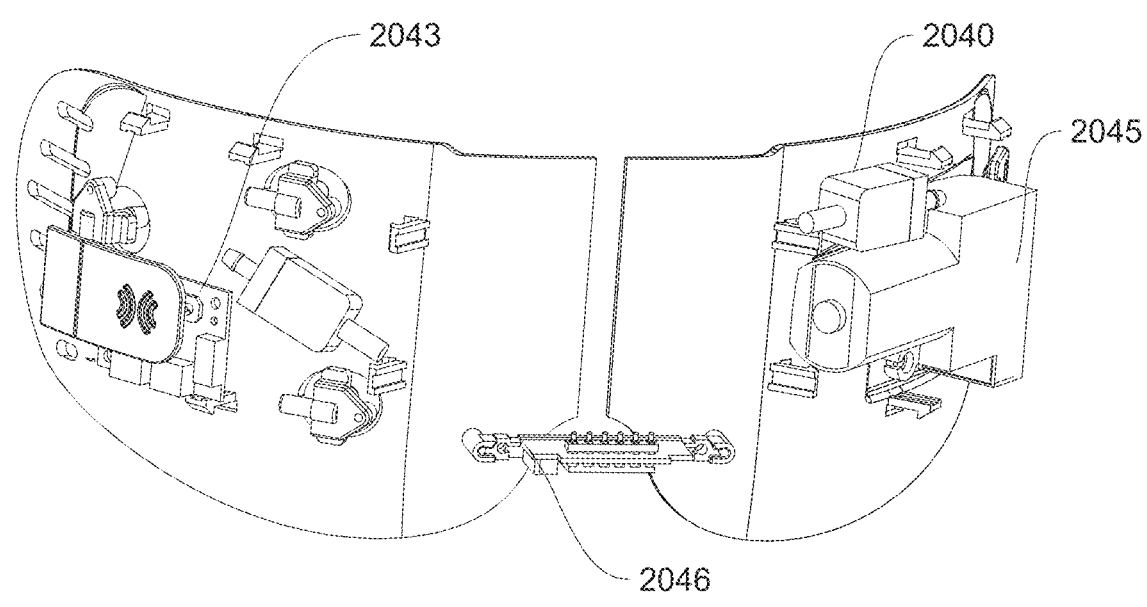
FIG. 16 is a structural schematic view of internal components of the massaging assembly according to an embodiment of the present disclosure.
Figure 17:
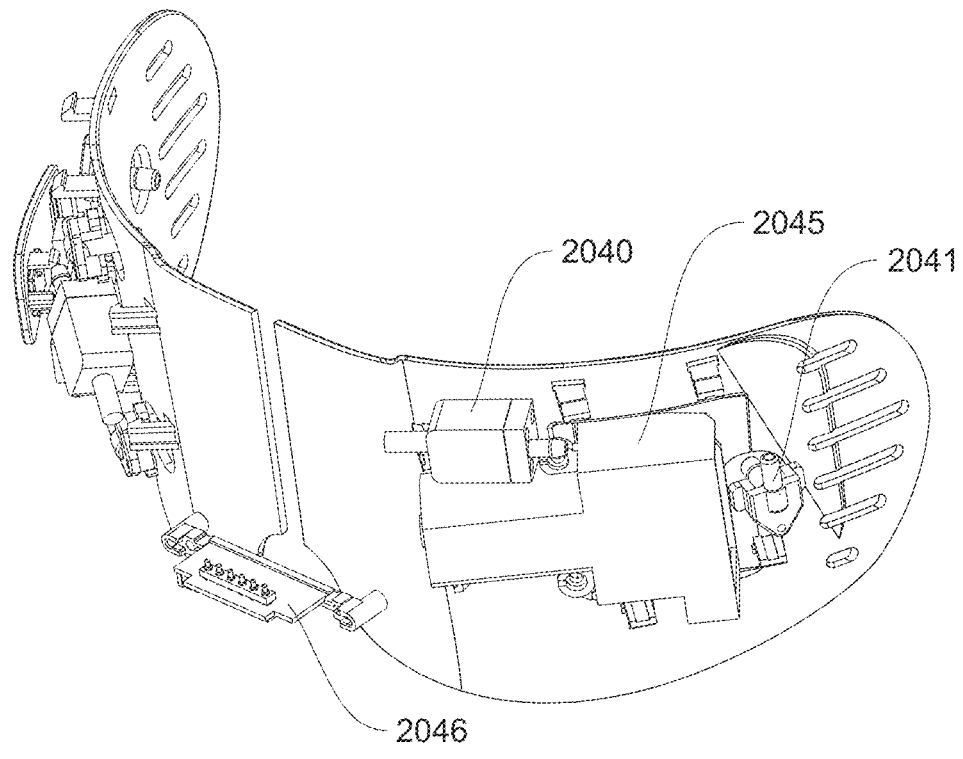
FIG. 17 is another structural schematic view of the internal components of the massaging assembly according to an embodiment of the present disclosure.

In an embodiment, as shown in FIGS. 7A to 7F, the power module 106 includes a first shell 1062, a battery 1064, a first PCBA board 1066, and an ejecting post base 1068. Specifically, the ejecting post base 1068 is disposed at a bottom of the first shell 1062 and passes through the bottom of the first shell 1062 to be electrically connected to the first PCBA board 1066 (as shown in FIG. 10). As shown in FIG. 10, the battery 1064 is electrically connected to the first PCBA board 1066. The battery 1064 and the first PCBA board 1066 are both disposed inside the first shell 1062. As shown in FIGS. 12 and 16, the air bag drive module 204 includes a second shell 2042, a power supply adapter PCBA board 2046, and a ejecting post set 2048. Specifically, the ejecting post set 2048 is arranged on and passes through the second shell 2042 to be electrically connected to the power supply adapter PCBA board 2046. In an example, the ejecting post set 2048 is an ejecting post connector. When the power supply module 106 is received in the recess 206 of the air bag drive module 204, the ejecting post set 2048 is electrically connected with the ejecting post base 1068.

Figure 7A:
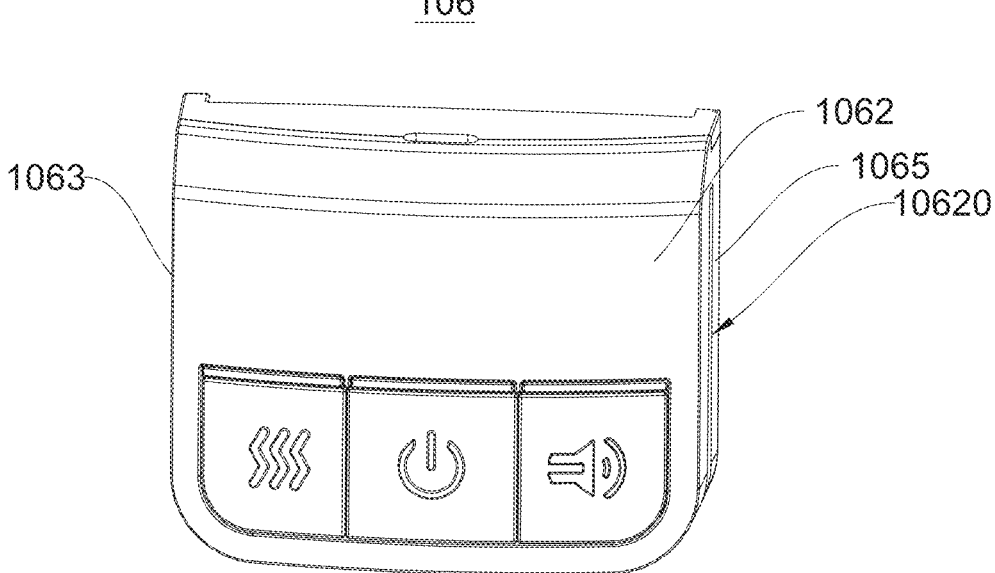
FIG. 7A is a first structural schematic view of a power supply module of the eye mask assembly shown in FIG. 2.
Figure 14:
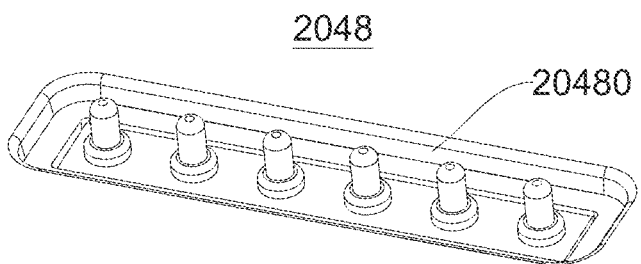
FIG. 14 is a structural schematic view of an ejecting post set shown in FIG. 12.

In an embodiment, a flange 10680 (shown in FIG. 7G) is arranged surrounding the ejecting post base 1068, and a concave edge 20480 (shown in FIG. 14) is arranged surrounding the ejecting post set 2048. When the eye massager 100 is in the assembled state, the ejecting post set 2048 and the ejecting post base 1068 form a hanging force via the flange 10680 and the concave edge 20480 to improve stability of connection between the power supply module 106 and the air bag drive module 204.

Figure 7B:
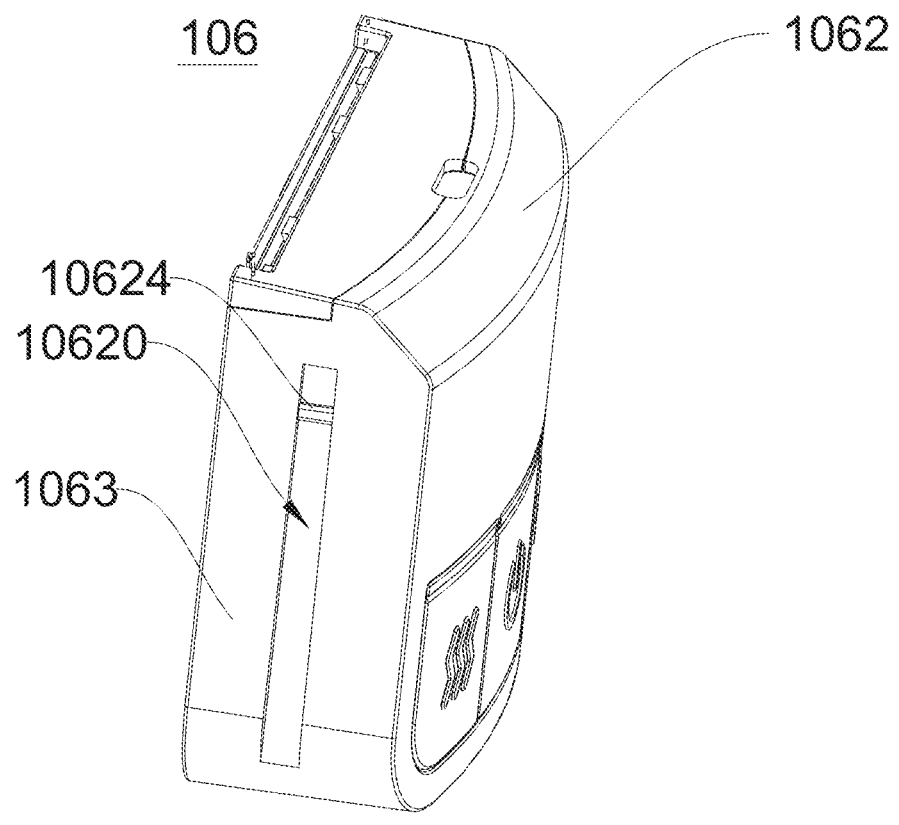
FIG. 7B is a second structural schematic view of the power supply module of the eye mask assembly shown in FIG. 2.
Figure 7C:
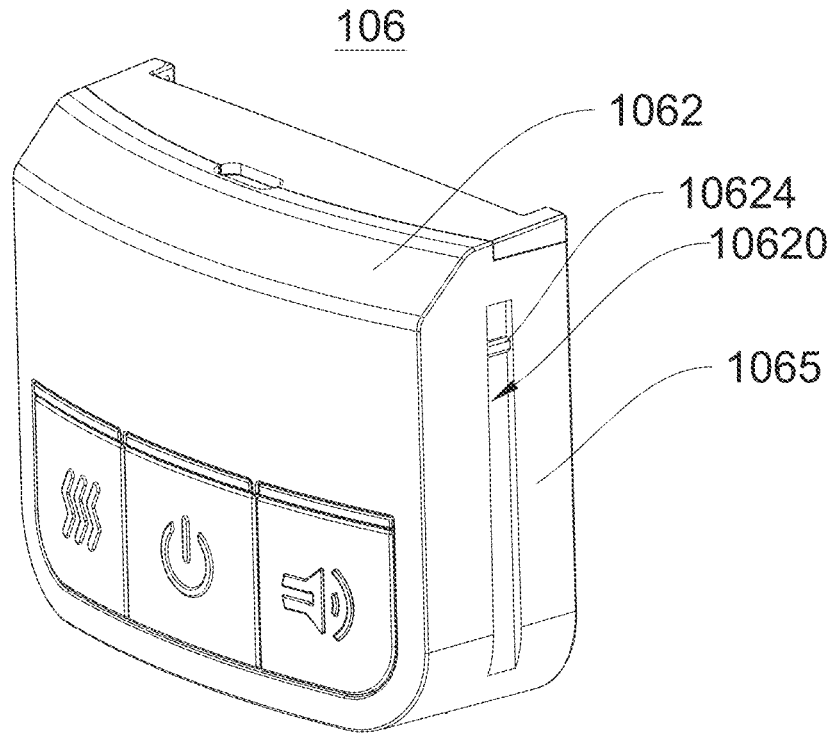
FIG. 7C is a third structural schematic view of the power supply module of the eye mask assembly shown in FIG. 2.
Figure 13:
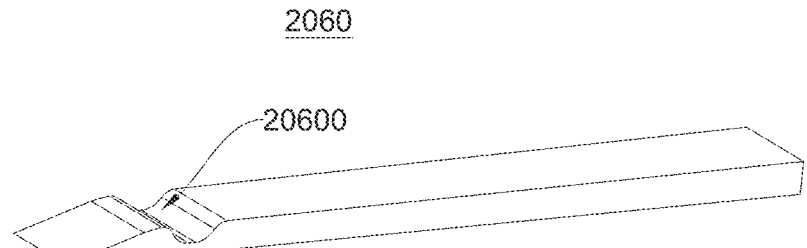
FIG. 13 is a structural schematic view of a guiding protrusion shown in FIG. 12.

In an embodiment, guiding protrusions 2060 (shown in FIGS. 12 and 13) are provided on each of two side walls of the recess 206 correspondingly. Guide grooves 10620 (shown in FIGS. 7A to 7C) are defined in two sides of the first shell 1062. The first shell 1062 is slidably and detachably arranged in the recess 206 via the guide grooves 10620 and the guiding protrusions 2060. As shown in FIG. 7B and FIG. 7C, each guide groove 10620 is arranged with a protruding portion 10624. As shown in FIG. 13, each guiding protrusion 2060 defines a recess opening 20600. When the first shell 1062 is received in the recess 206, the protruding portion 10624 abuts against the recess opening 20600, further improving stability of the connection between the power supply module 106 and the air bag drive module 204.

In an embodiment, as shown in FIG. 12, the recess 206 is formed by a rear side wall 2062, a bottom wall 2064, a left side wall 2066 and a right side wall 2068. A top side 2061 and a front side 2063 of the recess 206 are opened. The guiding protrusions 2060 are respectively arranged on the left side wall 2066 and the right side wall 2068. The first shell 1062 slidably enters the recess 206 from the top side 2061 of the recess 206 via the guide grooves 10620 and the guiding protrusions 2060. The ejecting post set 2048 is arranged on the bottom wall 2064. Therefore, by arranging the guide grooves 10620 and the guiding protrusions 2060, when the power supply module 106 is fixed in the recess 206, a restricting force is applied from two sides of the recess 206, ensuring the eye mask assembly 10 and the massaging assembly 20 of the eye massager 100 to be assembled stably.

Figure 7D:
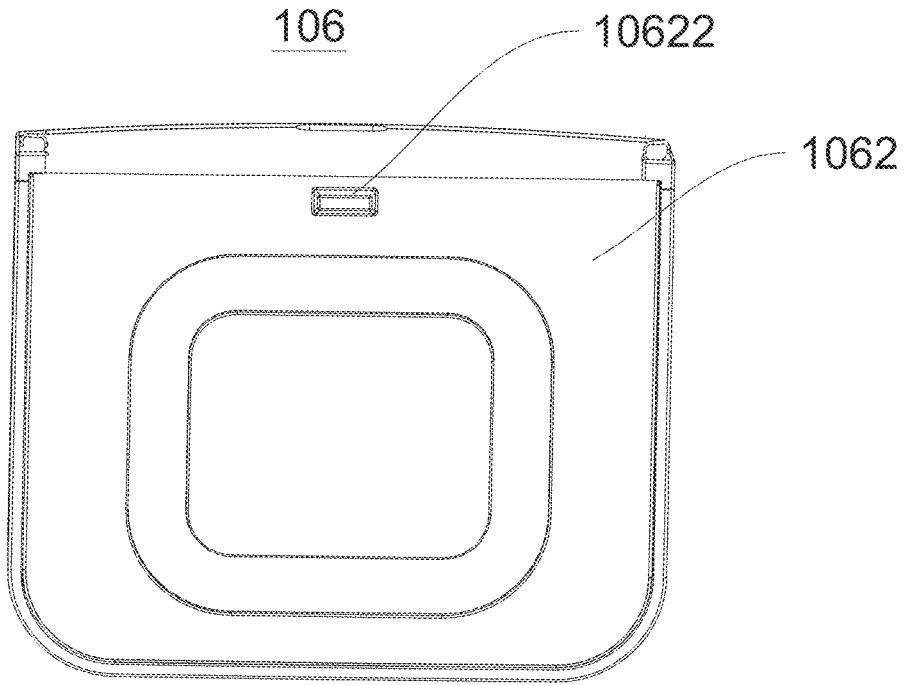
FIG. 7D is a fourth structural schematic view of the power supply module of the eye mask assembly shown in FIG. 2.
Figure 7E:
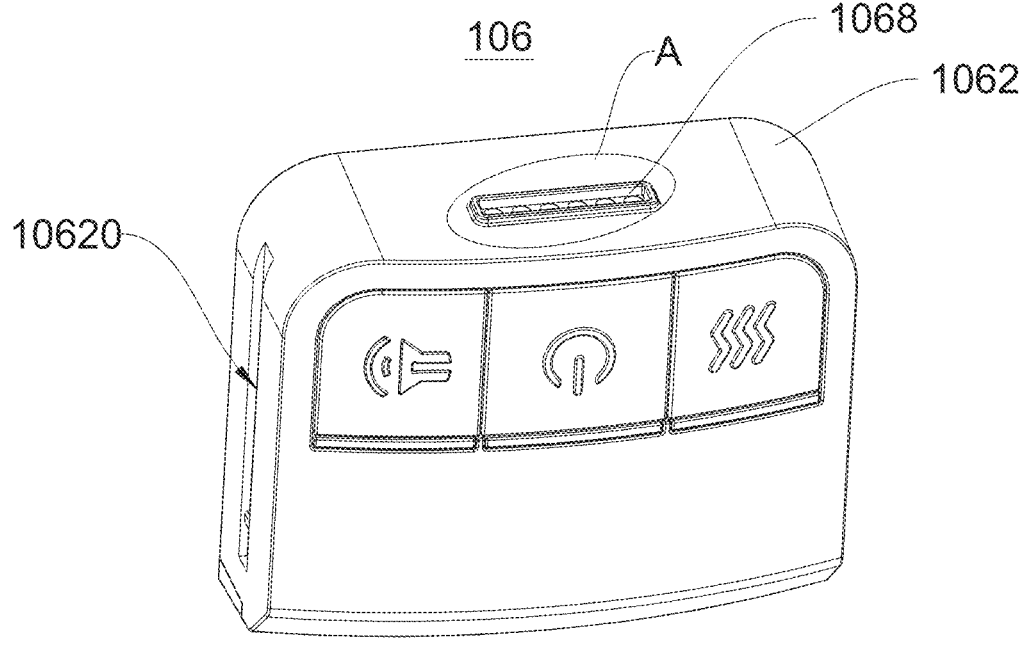
FIG. 7E is a fifth structural schematic view of the power supply module of the eye mask assembly shown in FIG. 2.
Figure 7F:
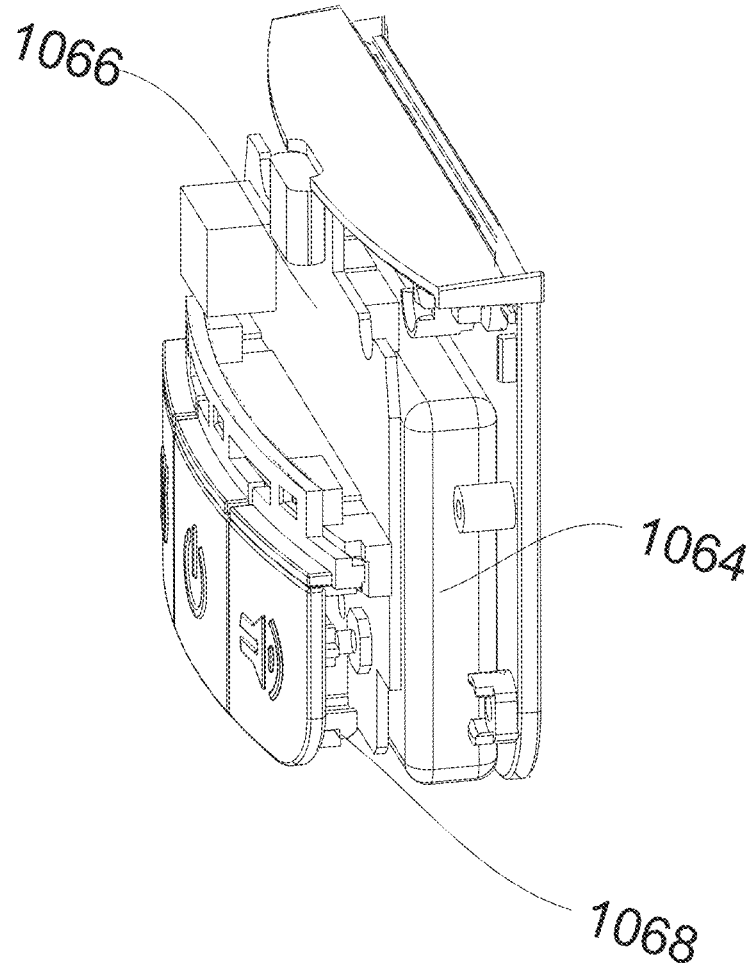
FIG. 7F is a structural schematic view of an interior of the power supply module of the eye mask assembly shown in FIG. 2.
Figure 7G:
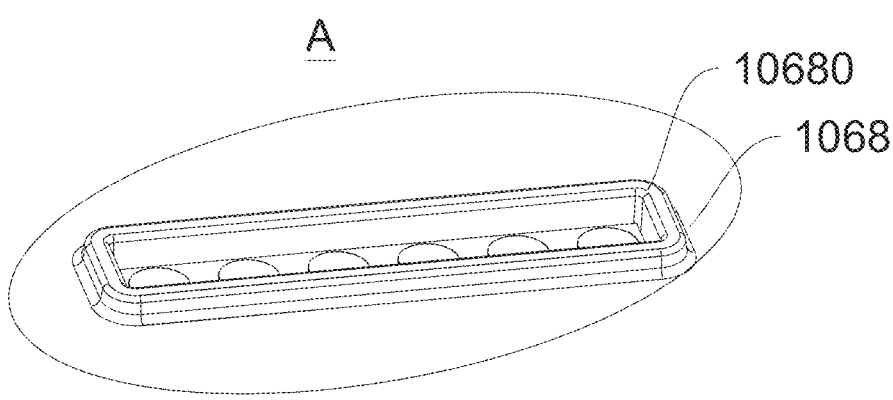
FIG. 7G is an enlarged view of a region A shown in FIG. 7E.

Further, as shown in FIG. 12, a snap slot 2065 is defined in the rear side wall 2062 and is disposed near the top side 2061. As shown in FIG. 7D, a protrusion 10622 is arranged on the first shell 1062 corresponding to the snap slot 2065, i.e., at a rear side of the power supply module 106. When the first shell 1062 is received in the recess 206, the protrusion 10622 is snapped into the snap slot 2065. In this way, in the present embodiment, by arranging the recess 206 and the protrusion 10622 in addition to the guiding protrusions 2060, the guide grooves 10620, the ejecting post set 2048 and the ejecting post base 1068, the power supply module 106 and the air bag drive module 204 are restricted from four directions (left, right, down, and inside), further ensuring stability of assembling between the eye mask assembly 10 and the massaging assembly 20 of the eye massager 100.

Figure 9:
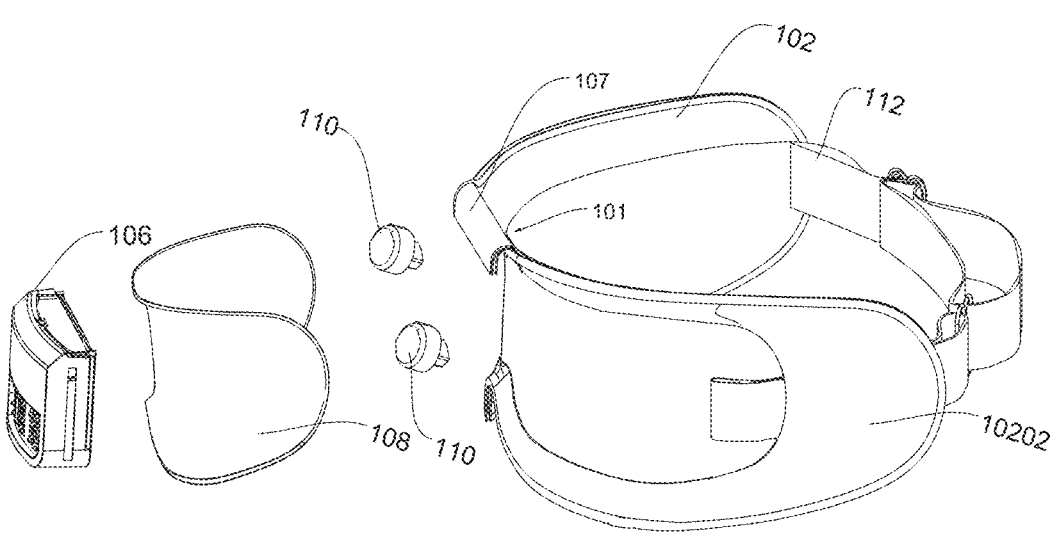
FIG. 9 is a structural schematic view of the eye mask assembly after being disassembled according to still another embodiment of the present disclosure.

In an embodiment, as shown in FIG. 9, the eye mask assembly 10 further includes a heating structure 108. The heating structure 108 is arranged inside the flexible eye mask body 102 to generate heat to provide a comfortable temperature for the eyes of the user. As shown in FIG. 10, the first PCBA board 1066 is electrically connected to the heating structure 108. The heating structure can be used independently from the massaging assembly 20, and the user can use the heating function when using the eye mask assembly 10 alone to provide the comfortable temperature to the eyes, which is more helpful to the eyes of the user. In an example, the heating structure 108 may be an electric heating sheet or may be configured as other structures. The present disclosure does not specifically limit a structure of the heating structure 108. In addition, as shown in FIG. 9, the eye mask assembly 10 may include two speakers 110. Each of the two speakers 110 is arranged in an interlayer 10202 of the respective one pocket structure 1020 to play a control command or music. Specifically, as shown in FIG. 10, the speakers 110 are electrically connected to the first PCBA board 1066. In some embodiments, the eye mask assembly 10 may further include a Bluetooth module (not shown in the drawings) to achieve communicative connection with an external device. The user may take the Bluetooth module to play sleep-aiding music while using the eye mask assembly 10. As shown in FIGS. 7A-7C, the power module 106 further includes a charging interface. The battery 1064 is a rechargeable battery, and the charging interface is configured to charge the battery 1064.

Figure 18:
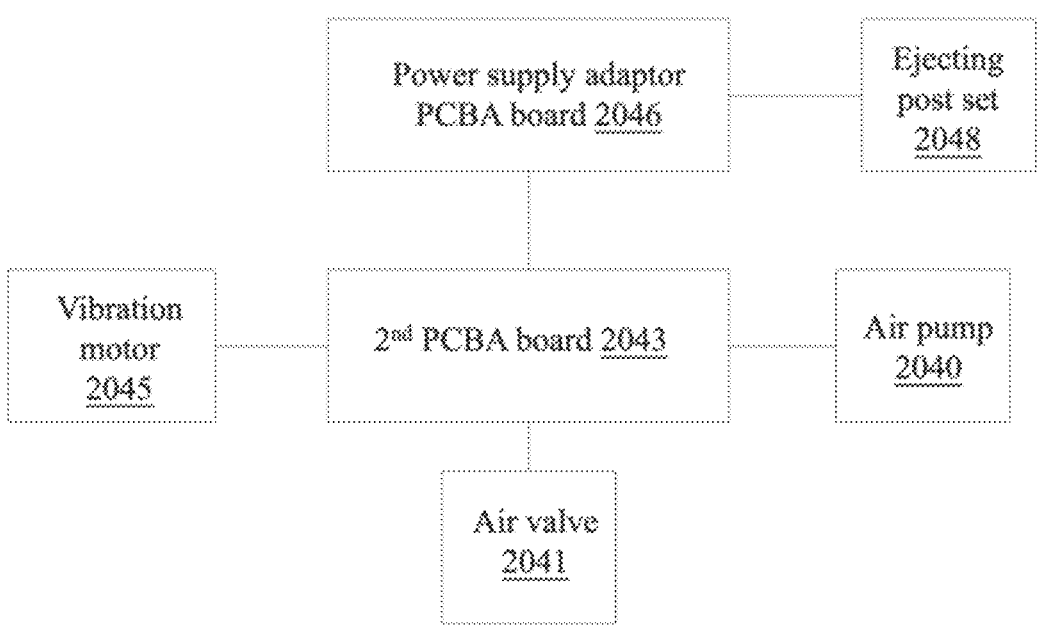
FIG. 18 is a structural schematic view of connection between the internal components of the massaging assembly according to an embodiment of the present disclosure.

As shown in FIGS. 15-18, the air bag drive module 204 further includes an air pump 2040, an air valve 2041, a second PCBA board 2043, and a vibration motor 2045 arranged in the second shell 2042. As shown in FIG. 18, the power supply adapter PCBA board 2046 is electrically connected to the second PCBA board 2043; and the air pump 2040, the air valve 2041, and the vibration motor 2045 are electrically connected to the second PCBA board 2043. The air pump 2040 and the air valve 2041 inflate and deflate the air bag 2022 to perform pressurized massaging. The vibration motor 2045 is configured to perform vibrating massaging.

In an embodiment, as shown in FIG. 3, the eye mask assembly 10 further includes a fixing strap 112, the flexible eye mask body 102 and the fixing strap 112 cooperatively define a ring-shaped structure to enable the flexible eye mask body 102 to sleeve the eyes of the user. A length of the fixing strap 112 is adjustable. For example, the length may be adjusted via an adjustment clasp in FIG. 3. In an example, the fixing strap 112 may be an elastic or fabric strap.

In an embodiment, as shown in FIG. 4, a cushioning portion 114 is extending along a lower edge 1025 of the flexible eye mask body 102. The cushioning portion is protruding towards the eyes and a nose bridge of the user to reduce a pressure applied to the user due to a weight of the eye massager 100.

In addition, it is understood that the foregoing embodiments are only exemplary illustration of the present disclosure, and as long as there is no conflict in the technical features, no contradiction in the structure, and no departing from of the concept of the present disclosure, the technical solutions of various embodiments may be used in any combination and cooperation.

Obviously, the above-described embodiments show only a part of, not all of, the embodiments of the present disclosure. The accompanying drawings provide preferred embodiments of the present disclosure without limiting the scope of the present disclosure. The present disclosure may be achieved in various forms. These embodiments are provided for understanding the present disclosure more thoroughly and comprehensively. Although the present disclosure has been described in detail by referring to the foregoing embodiments, any ordinary skilled person in the art may modify the technical solutions in the foregoing specific embodiments or may perform equivalent substitutions for some of the technical features therein. Any equivalent structure made based on the contents of the specification and the accompanying drawings of the present disclosure, applied directly or indirectly in other related technical fields, shall all be within the scope of the present disclosure.

What is claimed is:

1. An eye massager, comprising:
an eye mask assembly, comprising a flexible eye mask body configured to cover eyes of a user to shield light from the eyes;
a massaging assembly, wherein the massaging assembly and the flexible eye mask body are detachably connected to each other and are selectively in an assembled state or a separate state; when the massaging assembly and the flexible eye mask body are in the assembled state, the eye massager is configured to massage at least one of: an eye region, an eye peripheral region, and temples of the user; and when the massaging assembly and the flexible eye mask body are in the separate state, the eye mask assembly is configured to be used without the massaging assembly and configured to cover the eyes;
wherein, the flexible eye mask body comprises a first body portion and a second body portion stacked on the first body portion; a pocket structure is formed between the first body portion and the second body portion;
two openings of the pocket structure face towards a middle portion of the flexible eye mask body;
when at least two first connection members and at least two second connection members are provided and are connected to each other correspondingly, a first side edge of the massaging assembly and a second side edge of the massaging assembly opposite to the first side edge are capable of being respectively at least partially inserted in the pocket structure through the two openings to be connected to the flexible eye mask body or are capable of being taken out of the pocket structure through the two openings to be separated from the flexible eye mask body.

2. The eye massager according to claim 1, wherein the flexible eye mask body and the massaging assembly are arranged transversely and are configured to be attached to the eyes of the user, extending along an extending direction;

the at least two first connection members are arranged on the flexible eye mask body along the extending direction; and
the at least two second connection members are arranged on the massaging assembly along the extending direction; the at least two first connection members and the at least two second connection members are detachably connected to each other in one-to-one correspondence to enable the eye mask assembly and the massaging assembly to be selectively in the assembled state or the separate state.

3. The eye massager according to claim 2, wherein a number of the at least two first connection members is two, and a number of the at least two second connection members is two;
the two first connection members are respectively disposed at a left side and a right side of the flexible eye mask body;
the two second connection members are respectively arranged on a left side and a right side of the massaging assembly;
one of the two first connection members is detachably connected to a respective one of the two second connection members, disposed on a same side as the one of the two first connection members, to enable the massaging assembly to be tightly attached to the flexible eye mask body.

4. The eye massager according to claim 2, wherein each of the at least two first connection members is a pullable strap, and each of the at least two second connection members is a pull ring having an opening; or
each of the at least two first connection members is a pull ring having an opening, and each of the at least two second connection members is a pullable strap.

5. The eye massager according to claim 1, wherein each of the at least two first connection members is respectively at least partially received in the pocket structure.

6. The eye massager according to claim 1, wherein the massaging assembly comprises:
an air bag module, disposed facing towards the flexible eye mask body, wherein the air bag module comprises a base and an air bag arranged in the base;
an air bag drive module, disposed on a first side of the air bag module away from the flexible eye mask body, wherein the air bag drive module is configured to inflate and deflate the air bag;
wherein the at least two second connection members are respectively arranged at a left side and a right side of the air bag drive module; an extending length of the base in an extending direction is greater than an extending length of the air bag drive module in the extending direction to enable each of a left end and a right end of the base to be inserted respectively in the pocket structure.

7. The eye massager according to claim 1, further comprising:
a first sticker, arranged on the flexible eye mask body; and
a second sticker, arranged on the massaging assembly, wherein the first sticker and the second sticker are disposed opposite to each other to enable the flexible eye mask body and the massaging assembly to be detachably adhered to each other.

8. The eye massager according to claim 7, wherein the first sticker is disposed at a middle portion of the flexible eye mask body, and the second sticker is disposed at a middle portion of the massaging assembly.

9. The eye massager according to claim 1, wherein the eye mask assembly comprises two speakers; each of the two speakers is respectively arranged in an interlayer of the pocket structure to play a control command or music.

10. The eye massager according to claim 1, wherein the eye mask assembly further comprises a fixing strap, the flexible eye mask body and the fixing strap cooperatively define a ring-shaped structure to enable the flexible eye mask body to sleeve the eyes of the user; and a length of the fixing strap is adjustable.

11. The eye massager according to claim 1, wherein a cushioning portion is configured to extend along a lower edge of the flexible eye mask body; the cushioning portion is configured to protrude towards the eyes and a nose bridge of the user to reduce a pressure applied to the user caused by a weight of the eye massager.

12. An eye massager, comprising:

an eye mask assembly, comprising a flexible eye mask body configured to cover eyes of a user to shield light from the eyes;

a massaging assembly, wherein the massaging assembly and the flexible eye mask body are detachably connected to each other and are selectively in an assembled state or a separate state; when the massaging assembly and the flexible eye mask body are in the assembled state, the eye massager is configured to massage at least one of: an eye region, an eye peripheral region, and temples of the user; and when the massaging assembly and the flexible eye mask body are in the separate state, the eye mask assembly is configured to be used without the massaging assembly and configured to cover the eyes;

wherein, the flexible eye mask body is arranged with a connection portion, the massaging assembly defines a power supply receiving space; a power supply module is detachably received in the power supply receiving space;

when the power supply module is received in the power supply receiving space and the massaging assembly and the flexible eye mask body are in the assembled state, the power supply module is electrically connected to the massaging assembly and is connected to the flexible eye mask body via the connection portion to supply power for a heating structure arranged inside the flexible eye mask body; and when the massaging assembly and the flexible eye mask body are in the separate state and the power supply module is connected to the flexible eye mask body via the connection portion, the power supply module is configured to supply power for the heating structure arranged inside the flexible eye mask body.

13. The eye massager according to claim 12, wherein, the massaging assembly comprises an air bag module and an air bag drive module; the air bag module comprises a base and an air bag arranged in the base; the air bag drive module is configured to inflate and deflate the air bag;

the air bag drive module defines a recess; the power supply module is detachably received in the recess to be electrically connected to the air bag drive module;

the power supply module comprises a first shell, a battery, a first PCBA board, and an ejecting post base; the battery is electrically connected to the first PCBA board; the ejecting post base is arranged on the first shell and passes through the first shell to be electrically connected to the first PCBA board;

the air bag drive module comprises a second shell, a power supply adapter PCBA board, and an ejecting post set; the ejecting post set is arranged on and passes through the second shell to be electrically connected to the power supply adapter PCBA board; and when the power supply module is received in the recess of the air bag drive module, the ejecting post set is electrically connected with the ejecting post base.

14. The eye massager according to claim 13, wherein, a flange is arranged surrounding the ejecting post base, and a concave edge is arranged surrounding the ejecting post set; and when the ejecting post set is electrically connected to the ejecting post base, the flange snaps with the concave edge.

15. The eye massager according to claim 14, wherein the recess is defined in the second shell; guide grooves are respectively defined in two sides of the first shell; guiding protrusions are respectively arranged on two side walls of the recess; the first shell is slidably and detachably arranged in the recess via the guide grooves and the guiding protrusions.

16. The eye massager according to claim 15, wherein the recess is formed by a rear side wall, a bottom wall, a left side wall and a right side wall; a top side and a front side of the recess are opened; the guiding protrusions are respectively arranged on the left side wall and the right side wall; the first shell slidably enters the recess from the top side of the recess via the guide grooves and the guiding protrusions.

17. The eye massager according to claim 16, wherein the ejecting post set is arranged on the bottom wall; a snap slot is defined in the rear side wall and is disposed near the top side; a protrusion is arranged on the first shell corresponding to the snap slot; when the first shell is received in the recess, the protrusion is snapped into the snap slot.

18. The eye massager according to claim 13, wherein the heating structure is arranged inside the flexible eye mask body to generate heat to provide a comfortable temperature for the eyes of the user; the first PCBA board is electrically connected to the heating structure.

19. The eye massager according to claim 13, wherein the air bag drive module further comprises an air pump, an air valve, a second PCBA board, and a vibration motor arranged in the second shell;

the power supply adapter PCBA board is electrically connected to the second PCBA board; and the air pump, the air valve, and the vibration motor are electrically connected to the second PCBA board;

the air pump and the air valve are configured to inflate and deflate the air bag to perform pressurized massaging, the vibration motor is configured to perform vibrating massaging.

\* \* \* \* \*